(12) United States Patent
Tanaka et al.

(10) Patent No.: US 8,211,678 B2
(45) Date of Patent: Jul. 3, 2012

(54) ETHANOL PREPARATION METHOD

(75) Inventors: Akihisa Tanaka, Wako (JP); Kazuhiro Kagawa, Wako (JP); Pu Qian, Wako (JP)

(73) Assignee: Honda Motor Co., Ltd., Tokyo (JP)

( * ) Notice: Subject to any disclaimer, the term of this patent is extended or adjusted under 35 U.S.C. 154(b) by 420 days.

(21) Appl. No.: 12/502,522

(22) Filed: Jul. 14, 2009

(65) Prior Publication Data

US 2010/0009422 A1    Jan. 14, 2010

(30) Foreign Application Priority Data

Jul. 14, 2008 (JP) ................................ 2008-182866
Apr. 22, 2009 (JP) ................................ 2009-103760

(51) Int. Cl.
*C12P 7/06* (2006.01)

(52) U.S. Cl. ..................................................... 435/161

(58) Field of Classification Search .................. None
See application file for complete search history.

(56) References Cited

FOREIGN PATENT DOCUMENTS

| JP | 7-185275 | 7/1995 |
|---|---|---|
| JP | 2006-88136 | 4/2006 |

OTHER PUBLICATIONS

Hamelinck et al., Biomass and Bioenergy, 2005, vol. 28, p. 384-410.*
Vane L. M., Journal of Chemical Technology and Biotechnology, 2005, vol. 80, p. 603-629.*
Zhou et al., Journal of Membrane Science, 1996, vol. 117, p. 303-309.*

* cited by examiner

*Primary Examiner* — Kade Ariani
(74) *Attorney, Agent, or Firm* — Nelson Mullin Riley & Scarborough LLP; Anthony A. Laurentano

(57) ABSTRACT

Provided is a method for preparing ethanol in high efficiency. The ethanol preparation method includes a step of yielding a saccharide water solution through saccharification of cellulose with an enzyme in water, a step of condensing the saccharide water solution, and a step of yielding an ethanol water solution by fermenting the saccharide in the condensed saccharide water solution into ethanol, wherein the step of condensing the saccharide water solution is performed through a pervaporation treatment on the saccharide water solution by using a water separation membrane composed of polypyrrole doped with a sulfonate ion.

2 Claims, 2 Drawing Sheets

ETHANOL PREPARATION METHOD

BACKGROUND OF THE INVENTION

1. Field of the Invention

The present invention relates to an ethanol preparation method in which a biomass containing cellulose is used as a raw material.

2. Description of the Related Art

In recent years, from the viewpoint of preventing global warming, it has been called on to reduce emission amount of carbon dioxide which is considered to be one of the reasons of global warming. Therefore, there has been considered to use a mixed fuel of ethanol and a liquid hydrocarbon compound such as gasoline as a vehicle fuel. The ethanol can be yielded from fermentation of a plant material, for example, an agricultural crop such as sugar cane, corn or the like. Since the plant itself, the raw material of the plant material, has absorbed carbon dioxide via photosynthesis, even though the ethanol produced from the plant material is combusted, the emission amount of carbon dioxide is equal to the amount of carbon dioxide absorbed by the plant itself. In other words, the summed emission amount of carbon dioxide can be made theoretically equal to zero, which is the so-called carbon neutral effect. Therefore, the emission amount of carbon dioxide can be reduced in accordance with the amount of ethanol which is used to replace the liquid hydrocarbon compound such as gasoline.

However, if sugar cane, corn and the like are consumed in a large amount as the raw materials for preparing ethanol, there is a problem that the amount thereof supplied as food would be decreased.

In this regard, there has been considered a technology to produce ethanol by using an inedible biomass containing cellulose as a substituent to the plant material such as sugar cane, corn or the like. As examples of the biomass containing cellulose, wood, rice straw, haulm, bagasse, bamboo, pulp and waste materials originated therefrom, such as waste paper, may be given.

As a preparation method for ethanol, there has been known a method as disclosed, for example, in Japanese Patent Laid-open No. 2006-88136, in which the biomass containing cellulose is saccharifized by enzyme to yield a saccharide solution, thereafter, saccharide contained in the saccharide solution is fermented into ethanol by introducing ethanol fermentative bacteria into the saccharide solution. The saccharification of the cellulose by enzyme is performed by, for example, adding the biomass containing the cellulose, together with water and diastase, into a mush tun. The ethanol fermentation of the saccharide solution is performed by, for example, introducing the saccharide water solution yielded in the mush tun into a fermentor and introducing the ethanol fermentative bacteria into the saccharide water solution.

In the saccharification (glycosylation) of cellulose by enzyme, the enzyme activity decreases as the concentration of glucose yielded according to the saccharification increases. Thereby, in order to prevent the enzyme activity from decreasing, it is favorable to maintain the glucose concentration of the saccharide water solution in the mush tun equal to or less than 10 w %, more favorably, equal to or less than 5 w %.

On the other hand, in order to accelerate the ethanol fermentation of the glucose, it is desirable that the glucose concentration of the saccharide water solution is within a range of 15 to 20 w %. Therefore, it is necessary to condense preliminarily the saccharide water solution yielded according to the saccharification of cellulose by enzyme so that the glucose concentration is within the mentioned range prior to the ethanol fermentation of the saccharide water solution. Generally, distillation method is adopted to condense the saccharide water solution.

However, large amount of heat energy is needed to condense the saccharide water solution according to the distillation method, therefore, it is disadvantageous.

SUMMARY OF THE INVENTION

The present invention has been accomplished in view of the aforementioned problems, and it is therefore an object of the present invention to provide a method for preparing ethanol in high efficiency.

To accomplish an object described above, the ethanol preparation method of the present invention includes a step of yielding a saccharide water solution through saccharifying a cellulose with an enzyme in water, a step of condensing the saccharide water solution, and a step of yielding an ethanol water solution by fermenting a saccharide contained in the condensed saccharide water solution into ethanol, wherein the step of condensing the saccharide water solution is performed through a pervaporation treatment on the saccharide water solution by using a water separation membrane composed of polypyrrole doped with a sulfonate ion.

Since the water separation membrane of the present invention is made of polypyrrole doped with a sulfonate ion, it can permeate water selectively. Thus, by performing the pervaporation treatment in which the water separation membrane is used on the saccharide water solution, water can be separated from, for example, the saccharide water solution of 5 w % at room temperature in high efficiency. Therefore, according to the ethanol preparation method of the present invention, it is possible to condense the saccharide water solution without the supply of heat energy, and accordingly, preparing ethanol in high efficiency.

However, the ethanol water solution yielded from fermentation of the saccharide contained in the saccharide water solution is dilute, since the ethanol concentration thereof is from 0.5 to 5 w %, for example. Therefore, it is necessary to further condense the ethanol water solution in order to use it as a liquid fuel.

Generally, distillation method is adopted as a condensation treatment on the ethanol water solution. However, when the concentration of ethanol reaches about 96 w %, ethanol and water are formed into an azeotrope; therefore, it is principally impossible to condensate the ethanol water solution further than 96 w % through the distillation method.

In this regard, there has been known a method as disclosed, for example, in Japanese Patent Laid-open No. H07-185275, in which ethanol is yielded in a concentration of more than 99 w % by separating water from the distillated ethanol water solution according to a pervaporation method. The pervaporation method adopts, for example, a zeolite water separation membrane to separate water from the ethanol water solution at a treatment temperature ranged from 50 to 75° C.

However, according to the conventional condensation treatment for the ethanol water solution, two steps of distillation and pervaporation are necessary.

As the condensation treatment for the ethanol water solution, there also has been known a method to yield ethanol in a concentration of more than 99 w % through azeotropic distillation using benzene. In the azeotropic distillation, benzene is needed as an azeotropic compound.

In this regard, it is favorable for the ethanol preparation method of the present invention to include a step of condensing the ethanol water solution which is performed through a pervaporation treatment on the ethanol water solution by using a water separation membrane composed of polypyrrole doped with a sulfonate ion.

According to the pervaporation treatment using the water separation membrane, the water can be separated in high efficiency from, for example, the ethanol water solution of 5 w % at room temperature. Therefore, according to the ethanol preparation method of the present invention, the ethanol water solution can be condensed in high efficiency through the pervaporation treatment using the water separation membrane.

The pervaporation treatment is performed by reducing a pressure on a permeation side of the water separation membrane by a vacuum pump to separate water in the saccharide water solution or the ethanol water solution supplied from a supply side thereof through the water separation membrane. In the pervaporation treatment, even though the vacuum pump is stopped, the water can be separated from the saccharide water solution or the ethanol water solution through the water separation membrane as long as a pressure difference between the supply side and the permeation side is maintained in a given range.

Thereby, it is favorable to stop the vacuum pump and maintain the pressure on the permeation side in a given range when the pressure on the permeation side is equal to or less than a given value in the ethanol preparation method of the present invention. According thereto, it is possible to reduce the driving time of the vacuum pump, and consequently, to reduce the energy consumed in preparing ethanol.

DETAILED DESCRIPTION OF THE PREFERRED EMBODIMENTS

Hereinafter, an embodiment of an ethanol preparation method of the present invention will be described further in detail with reference to the drawings.

In the ethanol preparation method of the present embodiment, naturally dried rice straws are used as a biomass containing cellulose.

Figure 1:
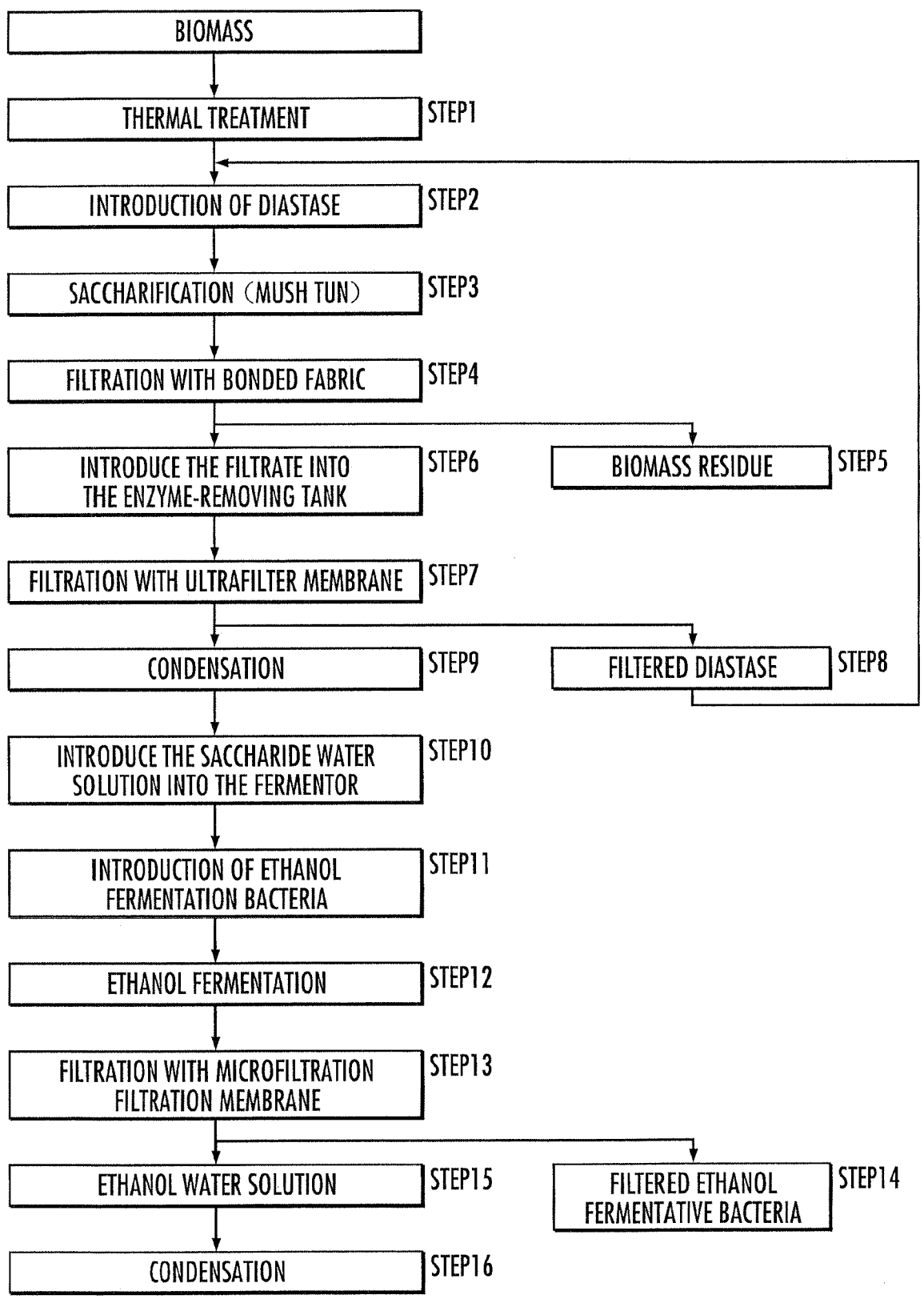
FIG. 1 is a flow chart illustrating steps of an ethanol preparation method according to the present invention.

According to the ethanol preparation method of the present embodiment, firstly, the rice straws are subjected to thermal treatment in STEP 1 illustrated in FIG. 1. As examples of the thermal treatment, thermal treatment by water vapor, thermal treatment by hot water and the like may be given. In the present embodiment, the thermal treatment is performed by water vapor.

The thermal treatment by water vapor can be performed in the following manner: the rice straws are put in, for example, a high-pressure boiler, water vapor of a temperature ranged from 200 to 220° C. is introduced into the high-pressure boiler, and the rice straws are heated under a temperature ranged from 180 to 200° C. for 15 to 60 mins.

In STEP 2, a commercially available diastase is introduced at a ratio of 10 w % with respect to the dried weight of the rice straws subjected to the thermal treatment by the water vapor. In the present embodiment, a kind of diastatic enzyme (commercial name: GC220) manufactured by Genencor Kyowa Co. Ltd. is used as the diastase. The diastase is a mixture of cellulase, hemicellulase and the like.

Thereafter, to the mixture of the rice straws and the diastase, acetate buffer and ion-exchanged water are added to yield an aqueous mixture with pH thereof at 4.5. The acetate buffer and the ion-exchanged water are added to adjust the aqueous mixture in such a manner that a ratio of the dried weight of the rice straws with respect to 1 L of the yielded aqueous mixture is 20 w/v %.

In STEP 3, cellulose contained in the aqueous mixture adjusted above is saccharified by the diastase to yield an enzyme-treated solution (saccharide water solution) containing saccharide. In detail, the aqueous mixture is introduced into the mush tun, and the saccharification (glycosylation) is performed at 50° C. for 24 hrs with stirring.

In STEP 4, the aqueous mixture after treated with enzyme in STEP 3 is filtered with a bonded-fiber fabric, for example.

According to the filtration, biomass residue resulted from the enzyme saccharification of the cellulose is filtered out and removed in STEP 5.

Meanwhile, filtrate yielded from the filtration is introduced into an enzyme-removing tank in STEP 6. Thereafter, in STEP 7, the filtrate introduced into the enzyme-removing tank is filtered with an ultrafilter membrane.

According to the filtration with the ultrafilter membrane, the diastase is filtered out of the filtrate and is removed in STEP 8. The diastase removed in STEP 8 is recovered and recycled by introducing the recovered enzyme again in STEP 2 as the diastase.

The saccharide water solution from which the diastase is removed in STEP 8 has a concentration, for example, around 5 w %. Thereafter, the saccharide water solution is condensed to a concentration ranged from 15 to 24 w % through a pervaporation treatment using a water separation membrane composed of polypyrrole doped with a sulfonate ion in STEP 9.

Figure 2:
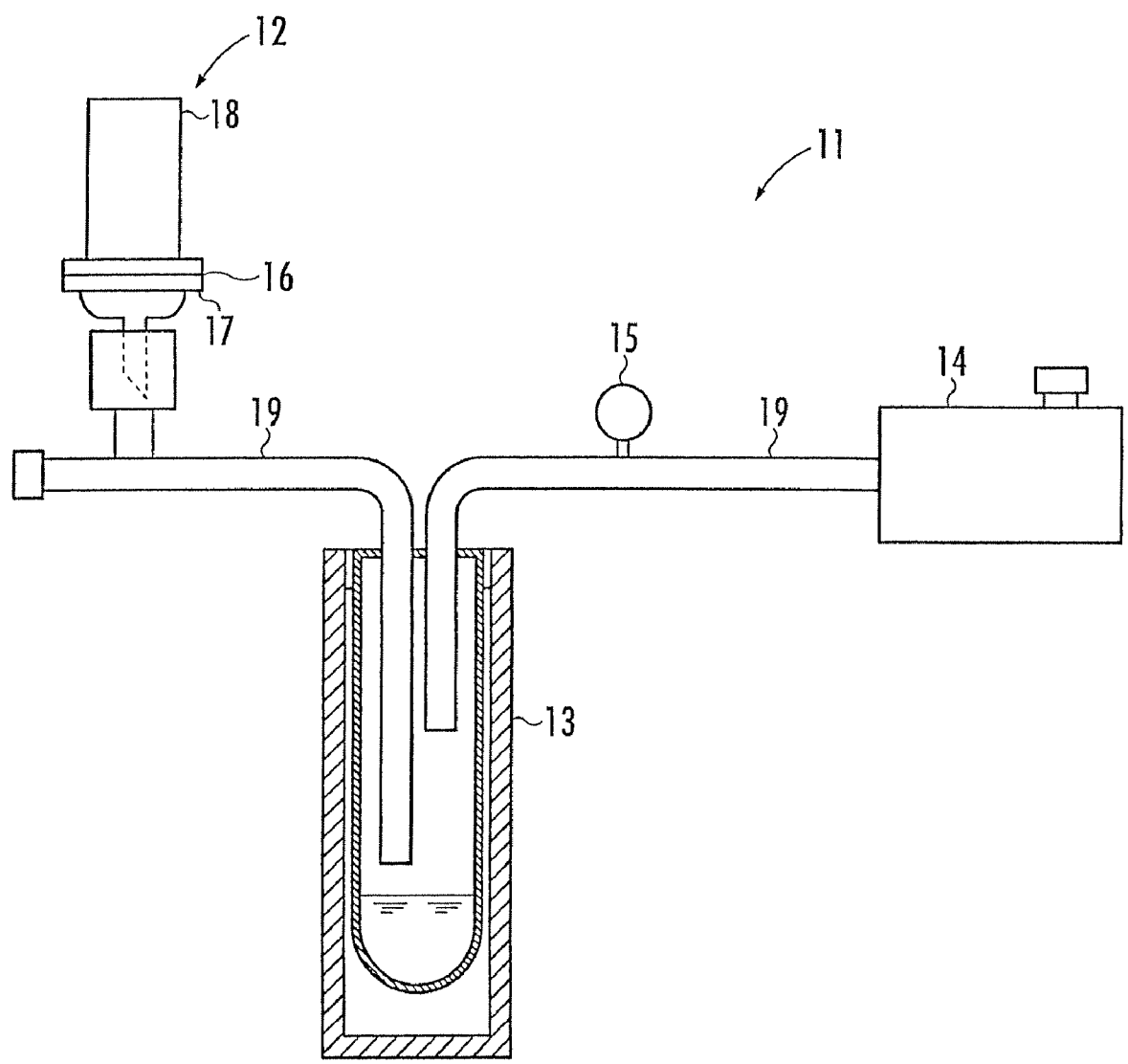
FIG. 2 is a structural view of a device used in pervaporation treatment.

In the present embodiment, the pervaporation treatment on the saccharide water solution is performed by using a pervaporation device 11 as illustrated in FIG. 2.

The pervaporation device 11 is provided with a pervaporation cell 12, a cold trap 13 which is cooled by liquid nitrogen, a vacuum pump 14, and a vacuum indicator 15. The pervaporation cell 12 has a sintered circular glass filter 16, a filter holder 17, and a cylindrical supply member 18 disposed upper of the filer holder 17. A lower end portion of the filter holder 17 is connected with a conduit 19. The conduit 19 is connected to the vacuum pump 14 through the cold trap 13. The vacuum indicator 15 is disposed between the cold trap 13 and the vacuum pump 14.

The sintered circular glass filter 16 allows vapor to permeate and has an effective permeation area of 346 mm² (diameter 21 mm). The upper side of the sintered circular glass filter 16 is disposed with a toroidal sealing member (not shown) made from Parafilm (registered trademark). The water separation membrane is formed into a circular shape with a diameter equal to an outer diameter of the sealing member and is disposed on the sealing member. The cylindrical supply member 18 is configured to accept the saccharide water solution. An inner circumferential side of the cylindrical supply member 18 is exposed with the water separation membrane.

The pervaporation treatment according to the pervaporation device 11 is performed by supplying the saccharide water solution to the cylindrical supply member 18, and the vacuum pump 14 is actuated to suction from the lower end portion side of the filter holder 17. As a result thereof, the condensed saccharide water solution can be yielded in the cylindrical supply member 18 by selectively separating water from the saccharide water solution. The separated water is trapped in the cold trap 13.

The water separation membrane used in the present embodiment is composed of polypyrrole doped with the sulfonate ion. Since polymers in the polypyrrole are bound with weak interacting Van der Waals force, it is easy for an ion to enter inside the polymers. Consequently, the polypyrrole can be doped by the sulfonate ion, which is an anion, under an oxidative condition. The polypyrrole doped with the sulfonate ion functions in the water separation membrane, selectively permeating water from a water solution of ethanol, saccharide or the like.

The sulfonate ion may be an aromatic sulfonate ion or an aliphatic sulfonate ion.

It is acceptable for the aromatic sulfonate ion to have a substituent group. It is desirable for the aromatic sulfonate ion to have a benzene ring or a naphthalene ring, a naphthalene ring is preferable. It is favorable for the aromatic sulfonate ion to have at least two sulfonate groups ($-SO_3^-$), more favorably at least three sulfonate groups, as the ionized sulfonic groups.

As examples of the aromatic sulfonate ion, the following substances of chemical formulas (1) to (10) may be given.

Chemical Formulas (1) to (10)

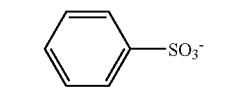

(1)

(2)

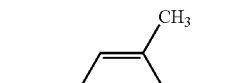

(3)

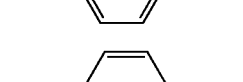

(4)

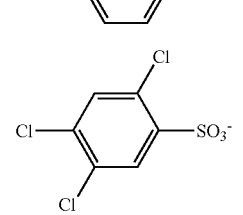

(5)

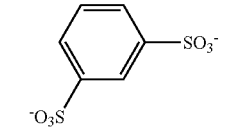

(6)

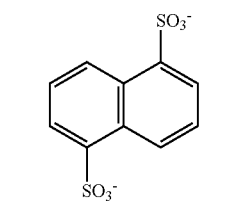

(7)

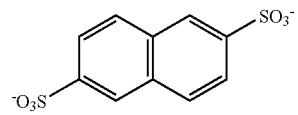

(8)

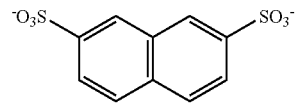

(9)

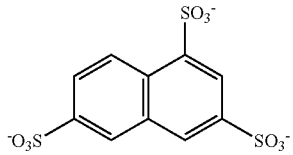

(10)

The aromatic sulfonate ion of chemical formula (1) is a benzene sulfonate ion, having a sulfonate group ($-SO_3^-$) in the benzene ring.

The aromatic sulfonate ion of chemical formula (2) is a p-toluene sulfonate ion, having a sulfonate group, and a p-methyl group relative to the sulfonate group as a substituent group in the benzene ring.

The aromatic sulfonate ion of chemical formula (3) is a 2,4-dimethyl benzene sulfonate ion, having a sulfonate group, and a p-methyl group and an o-methyl group relative to the sulfonate group as substituent groups in the benzene ring.

The aromatic sulfonate ion of chemical formula (4) is a 4-ethyl benzene sulfonate ion, having a sulfonate group and a p-ethyl group relative to the sulfonate group as a substituent group in the benzene ring.

The aromatic sulfonate ion of chemical formula (5) is a 2,4,5-trichloro benzene sulfonate ion, having a sulfonate group at position 1, and a chloro group at positions 2, 4 and 5, respectively, as a substituent group in the benzene ring.

The aromatic sulfonate ion of chemical formula (6) is a 1,3-benzene di-sulfonate ion, having a sulfonate group at positions 1 and 3, respectively, in the benzene ring.

The aromatic sulfonate ion of chemical formula (7) is a 1,5-naphthalene di-sulfonate ion, having a sulfonate group at positions 1 and 5, respectively, in the naphthalene ring.

The aromatic sulfonate ion of chemical formula (8) is a 2,6-naphthalene di-sulfonate ion, having a sulfonate group at positions 2 and 6, respectively, in the naphthalene ring.

The aromatic sulfonate ion of chemical formula (9) is a 2,7-naphthalene di-sulfonate ion, having a sulfonate group at positions 2 and 7, respectively, in the naphthalene ring.

The aromatic sulfonate ion of chemical formula (10) is a 1,3,6-naphthalene tri-sulfonate ion, having a sulfonate group at positions 1, 3 and 6, respectively, in the naphthalene ring.

As examples of the aliphatic sulfonate ion, the following substances of chemical formulas (11) and (12), respectively, may be given.

Chemical Formulas (11) and (12)

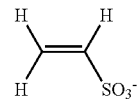

(11)

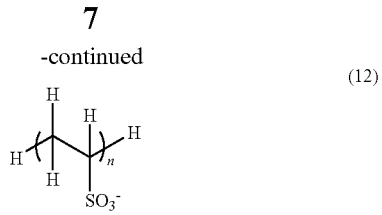

(12)

The aliphatic sulfonate ion of chemical formula (11) is a vinyl sulfonate ion, having a hydrogen atom in ethylene molecule substituted by the sulfonate group. The aliphatic sulfonate ion of chemical formula (12) is a polyvinyl sulfonate ion, having the vinyl sulfonate ion of chemical formula (11) as a constituent unit. In the chemical formula (12), the number n is desired to be in a range, for example, from 100 to 10,000.

The aliphatic sulfonate ion is favorably the vinyl sulfonate ion having chemical formula (11), more favorably, the polyvinyl sulfonate ion having chemical formula (12).

As illustrated in FIG. 1, the saccharide water solution condensed via the pervaporation treatment is introduced into a fermentor in STEP 10.

In STEP 11, 2 w % of the ethanol fermentative bacteria in wet weight with respect to the saccharide water solution introduced into the fermenter is added. In the present embodiment, Saccharomyces cerevisiae (yeast S288C strain (NBRC 1136)) is used as the ethanol fermentative bacteria.

In STEP 12, the saccharide contained in the saccharide water solution which has been introduced into the fermenter is fermented into ethanol to yield an ethanol fermentation solution containing ethanol (ethanol water solution). In detail, the ethanol is fermented by stirring the saccharide water solution introduced into the fermenter for 6 to 8 hrs at 30° C.

In STEP 13, the ethanol fermentation solution yielded in STEP 12 is filtered with a microfiltration membrane.

According to the filtration, the ethanol fermentative bacteria is filtered out and removed in STEP 14.

Meanwhile, in STEP 15, an ethanol water solution is yielded as the filtrate of the filtration. The ethanol water solution has a concentration ranged from 0.5 to 5 w %.

Therefore, in STEP 16, the ethanol water solution is condensed through pervaporation treatment using the water separation membrane composed of polypyrrole doped with the sulfonate ion. In the present embodiment, the pervaporation treatment on the ethanol water solution is performed by using the pervaporation device 11 illustrated in FIG. 2 in the same manner as the condensation of the saccharide water solution performed in STEP 9, except that the ethanol water solution is used in replace of the saccharide water solution.

Accordingly, the ethanol water solution can be yielded to have a concentration equal to or greater than 99 w % according to the present embodiment.

Hereinafter, an example will be given on the pervaporation treatment for the saccharide water solution performed in STEP 9.

In the present example, 6 to 20 g of the saccharide water solution yielded in STEP 8 was firstly supplied to the cylindrical supply member 18. The concentration of the saccharide water solution is 5 w %.

Thereafter, the vacuum pump 14 was actuated to suction from the lower end portion side of the filter holder 17 at room temperature (25° C.) to perform the pervaporation treatment for a sufficiently long time. After the pervaporation treatment, the saccharide concentration of the saccharide water solution remained in the cylindrical supply member 18 and the saccharide concentration of the liquid trapped in the cold trap 13 were measured. According to the amount and the saccharide concentration of liquid trapped in the cold trap 13, water permeation rate ($g/m^2 \cdot hr$) was calculated. The result thereof is shown in Table 1.

TABLE 1

| | | Supplied liquid | | Trapped liquid | |
| | | | After PV | After PV | |
| Supplied Weight (g) | Treatment Time (hr) | Before PV Saccharide Conc (w %) | Saccharide Conc (w %) | Saccharide Conc (w %) | W.P.R ($g/m^2 \cdot hr$) |
| --- | --- | --- | --- | --- | --- |
| 19.6 | 48.0 | 5 | 15.3 | 0 | 716.5 |
| 6.3 | 14.4 | 5 | 18.9 | 0 | 859.5 |
| 19.7 | 110.0 | 5 | 24.1 | 0 | 383.5 |

PV: Pervaporation;
W.P.R: Water permeation rate

It is obvious from Table 1 that the saccharide water solution remained in the cylindrical supply member 18 can be condensed to have a saccharide concentration ranged from 15.3 to 24.1 w % by performing the pervaporation treatment for a sufficiently long time, regardless of the amount of the saccharide water solution supplied to the cylindrical supply member 18. In addition, it is obvious that the trapped liquid in the cold trapper 13 located at the permeation side is water containing absolutely no saccharide.

According to the ethanol preparation method, the condensation treatment on the saccharide water solution in STEP 9 illustrated in FIG. 1 can be performed only through the pervaporation treatment at room temperature without undergoing distillation, and thus, it is clear that the ethanol can be prepared according thereto in high efficiency.

Hereinafter, an example of the pervaporation treatment on the ethanol water solution performed in STEP 16 will be given.

The pervaporation treatment in STEP 16 was performed in the same manner as the pervaporation treatment performed on the saccharide water solution, except that 5.5 g of ethanol water solution was supplied to the cylindrical supply member 18 in replace of the saccharide water solution. According to the amount and the ethanol concentration of liquid trapped in the cold trap 13, water permeation rate ($g/m^2 \cdot hr$) was calculated. The result thereof is shown in Table 2.

TABLE 2

| | | Supplied liquid | | Trapped liquid After PV | |
| Supplied Weight (g) | Treatment Time (hr) | Before PV EtOH Conc (w %) | After PV EtOH Conc (w %) | EtOH Conc (w %) | W.P.R ($g/m^2 \cdot hr$) |
| --- | --- | --- | --- | --- | --- |
| 5.5 | 45.3 | 0.5 | 99.01 | 0.09 | 669.8 |

PV: Pervaporation;
EtOH: Ethanol;
W.P.R: Water permeation rate

From Table 2, it is obvious that the ethanol water solution in the cylindrical supply member 18 can be condensed to at least 99 w % by performing the pervaporation treatment for a sufficiently long time. In addition, it is obvious that the trapped liquid in the cold trapper 13 located at the permeation side is substantially water containing no ethanol.

According to the ethanol preparation method of the present embodiment, the condensation treatment on the ethanol water solution in STEP 16 illustrated in FIG. 1 can be performed only through the pervaporation treatment at room temperature without undergoing distillation, and thus, it is clear that the ethanol can be prepared according thereto in high efficiency.

Further, in the ethanol preparation method of the present embodiment, the pervaporation treatment using the water separation membrane is performed on both the ethanol water solution and the saccharide water solution. Note that it is acceptable that the pervaporation treatment is performed on the saccharide water solution and the ethanol water solution may be condensed according to the other method.

Furthermore, in the ethanol preparation method of the present embodiment, the vacuum pump 14 has been driven to work regularly in the pervaporation treatment. Note that it is acceptable to stop the vacuum pump 14 when the pressure on the permeation side is equal to or less than a given value as long as the pressure on the permeation side is maintained in a given range.

What is claimed is:

1. A method of preparing ethanol comprising the steps of:
   (i) saccharifying a cellulose with an enzyme in water to yield a saccharide-water solution;
   (ii) condensing the saccahride-water solution, and;
   (iii) fermenting the condensed saccharide-water solution to yield an ethanol-water solution,
   wherein the condensing step is performed through a pervaporation treatment on the saccharide-water solution using a water separation membrane composed of polypyrrole doped with a sulfonate ion.

2. The method according to claim 1 further comprising a step of condensing the ethanol-water solution by pervaporation of the ethanol-water solution using the water-separation membrane composed of polypyrrole doped with the sulfonate ion.

* * * * *